United States Patent [19]

Tatsumi et al.

[11] Patent Number: 6,150,331
[45] Date of Patent: Nov. 21, 2000

[54] HUMAN GROWTH HORMONE-CONTAINING AQUEOUS PHARMACEUTICAL COMPOSITION

[75] Inventors: Masafumi Tatsumi, Kobe; Katsura Inoue, Akashi; Junichi Kajihara, Kobe, all of Japan

[73] Assignee: JCR Pharmaceuticals Co., Ltd., Hyogo-ken, Japan

[21] Appl. No.: 09/215,341

[22] Filed: Dec. 18, 1998

[30] Foreign Application Priority Data

Feb. 4, 1998 [JP] Japan .................................. 10-039609

[51] Int. Cl.[7] .................................................. A61K 38/27
[52] U.S. Cl. ..................... 514/12; 514/2; 514/8; 530/324; 530/351; 530/380; 530/395; 530/397; 530/399; 530/829; 435/69.1
[58] Field of Search ..................... 514/2, 12, 8; 530/324, 530/351, 380, 395, 397, 399, 829; 435/69.1

[56] References Cited

U.S. PATENT DOCUMENTS 5,763,394  6/1998  O'Connor et al. ........................ 514/12

FOREIGN PATENT DOCUMENTS

| 507497 | 10/1993 | Japan . |
| 508156 | 9/1994 | Japan . |
| 510031 | 11/1994 | Japan . |
| 509719 | 10/1995 | Japan . |
| 8-92125 | 4/1996 | Japan . |
| 92/00998 | 1/1992 | WIPO . |
| 93/03744 | 3/1993 | WIPO . |
| 93/19776 | 10/1993 | WIPO . |
| 94/03198 | 2/1994 | WIPO . |

OTHER PUBLICATIONS

Becker et al., Biotechnology and Applied Biochemistry, vol. 9, pp. 478–487 (1987).
Becker et al., Biotechnology and Applied Biochemistry, vol. 10, pp. 326–337 (1988).

Primary Examiner—F. T. Moezie
Attorney, Agent, or Firm—Greenblum & Bernstein, P.L.C.

[57] ABSTRACT

Provided is an aqueous pharmaceutical composition comprising human growth hormone wherein said human growth hormone is dissolved in a benzalkonium chloride-containing, slightly to weakly acidic solution buffered, most preferably, with maleate. The composition is sufficiently stable to be supplied in liquid state and can be prepared as a less painful composition.

38 Claims, No Drawings

HUMAN GROWTH HORMONE-CONTAINING AQUEOUS PHARMACEUTICAL COMPOSITION

FIELD OF THE INVENTION

The present invention relates to an injectable pharmaceutical preparation containing human growth hormone, and, in particular, to a pharmaceutical preparation in the form of a solution containing human growth hormone.

BACKGROUND OF THE INVENTION

Human growth hormone (abbreviated to "hGH") is a single chain polypeptide hormone, the naturally occurring type of which consists of 191 amino acid residues. hGH usually occurs in a biologically active monomer form, but is known to aggregate into dimers and then polymers under thermal stress or mechanical stress such as shaking imposed on its pharmaceutical preparation, leading to a loss of its biological activity (Becker, G. W. et al.(1987) Biotechnol. Appl. Biochem.,9, p.478).

On the other hand, it is known that long-term storage of a hGH aqueous solution causes a gradual production of a deamidation products while less forming polymerization products of hGH. The deamidated hGH, although having no alteration in its biological activity (Becker,G. W. et al.(1988) Biotechnol. Appl. Biochem., 10, p.326), is undesirable in a pharmaceutical product as its presence is thought to imply declining qualities, and its allowable content is thus usually provided by the specification.

It is also generally known that the denaturation of hGH by aggregation occurs mainly under physical stresses, while its denaturation by deamidation occurs mainly under chemical stresses.

Due to these problems, an optimal aqueous preparation of hGH has never been developed, and thus lyophilized preparations are common which are dissolved prior to injection.

As treatment with hGH to alleviate dwarfism takes a long period of years, self-injection is allowed and generally conducted at home from the start of its administration. When using a lyophilized preparation of hGH, the preparation is dissolved in an attached solvent and then injected subcutaneously or intramuscularly by the patient himself (usually a child) or his family members. Thus, it is the patient or his family members that carry out the dissolution procedure of the lyophilized preparation. Therefore, it is necessary for a physician in charge to give an adequate guidance as to how to dissolve it in order to avoid formation of aggregation products which leads to reduction of biological activity of the hGH. Their product inserts also contain cautions and instructions that hGH should be dissolved with a gentle circular motion.

As aggregates formation has also been noted in production steps of lyophilized preparations, various attempts have been made to suppress aggregates formation. However, there still are eager needs for development of more easily handled, stable preparations than the usual types of preparations which are dissolved prior to use. Recently, a kit type preparation with an associated syringe has come into use. But it has a complex structure so that dissolution of the lyophilized hGH is effected within the syringe, and it therefore makes it necessary to give especially careful and thorough explanation to the patient or his family on how to use it. Also, risks of unforeseeable erroneous handling cannot be cleared off.

As hGH is thus commonly injected at home by the patient or his family, provision of an aqueous form hGH preparation, in which dissolution procedure is eliminated, would promote convenience. Such a proper form of aqueous preparation would serve to ease the burden imposed on the patient and his family because it can be handled easily without the need of structurally complex devices employed in usual two-chamber type products requiring dissolution prior to use, e.g., a pen-type product including lyophilized hGH and a solvent which are separated by a partition.

There are following predominant patent applications addressed to hGH aqueous preparations.

CABI, in Unexamined Patent Publication No. 508156/1994 (hereinafter referred to as "CABI publication"), discloses an injectable composition of hGH or its active analogues with a pH of 5–7.5 and containing 2–50 mM citric acid as a buffering agent. It is stated in the same publication that better stability has been obtained by employing citrate than phosphate and that pH of about 6.0–7.0 is relatively preferable.

The above CABI publication teaches that the preparation set forth therein is stable for at least 12 months. In the same publication, however, "being stable" with regard to the monomer is defined as keeping the content not less than 85% of initial. Considering that specifications on the monomer content is generally considered to be not less than 90%, that preparation by CABI hardly seems to have sufficient stability.

On the other hand, through studies for improvement of quality and stability, the present inventors have also found, separately from the above disclosure by CABI, that pH is a crucial factor in the production of hGH preparation in the form of a solution, that use of a buffering agent which can maintain the preferable pH of 5–7, more preferable pH of 5.5–6.5, and that citrate, for example, is effective as such a buffering agent (Unexamined Patent Publication No. 92125/1996).

On the other hand, Genentech Inc. describes, in Unexamined Patent Publication No. 509719/1995 (hereinafter referred to as the "Genentech publication"), a liquid form hGH preparation comprising hGH, mannitol, a buffer and a nonionic surfactant. Citrate buffer is exemplified in that publication as being preferable.

Further, in Unexamined Patent Publication No. 507497/1993, Novo Nordisk Pharma describes a preparation which is produced first by crystallizing hGH by addition of acetone or ethanol in the presence of a divalent cation, e.g. $Zn^{2+}$, lyophilizing the crystals and putting the dried crystals into a pH 6.1–6.2 suspension comprising, e.g., phosphate, zinc acetate, glycerol, and benzylalcohol. In that publication, 6-month stability tests results at 22–24° C. are reported for the suspension made of hGH crystals, using ion-exchange HPLC for patterns of deamidation and decomposition and GPC for content of dimers and polymers, respectively. It is reported that even after 6 months the content of desamide products in the preparation was 5.0%, didesamide products 1.8%, dimers 1.2% and polymers 0.3% preparation, any of which were lower than the stability test results with the solutions reconstructed from usual lyophilized preparations. The same publication states that $Zn^{2+}$ is essential in crystallization to obtain large crystals. In addition, in spite that a water-soluble solvent such as acetone or ethanol is required in the crystallization of hGH, no mention is given to any alteration in secondary or higher structures of hGH crystals in the suspension, thus leaving points unclarified.

Acetone and ethanol are often used in purification of proteins to obtain them in precipitation. This method makes use of the lower solubility of proteins to organic solvents.

Though the concentration of such organic solvents in the same publication are lower than those used for making proteins precipitate, they would not be preferable for a pharmaceutical preparation administered to a human.

Upon this background, the present inventors pursued further research for an improved aqueous hGH preparation. In the process of our research, a variety of aqueous hGH preparations in liquid state were made using citrate buffer in accordance with what is described in the above unexamined patent publication by the present inventors and the CABI publication, and tests were conducted for their stability for a variety of time periods. It was then noted that any of these preparations developed slightly visible fine particles which were distinguished from aggregates. The fine particles were removable with a 0.22 μm filter, for example, but could be found again after a long-term storage or under such a stress as shaking. As formation of such fine particles would be problematic in quality with a pharmaceutical product, development of a new aqueous preparation was needed in which formation of such particles is suppressed.

On the other hand, while citrates are widely used in injectable preparations as buffering agents in slightly to weakly acidic conditions, it has been reported that they cause pain when the solution is injected subcutaneously or intramuscularly as is the case of the hGH (Unexamined Patent Publication No. 510031/94). The present inventors themselves also tested the preparations produced in accordance with the descriptions in the above CABI publication and above Unexamined Patent Publications by the present inventors, and found that these citrate-containing hGH injections cause substantial pain when the solution is infused.

Unlike stability problems of a preparation, the pain upon infusion is not a significant problem from the viewpoint of quality of the preparation. However, considering that a hGH preparation is injected on a frequent basis for a log period of time and that the patients of interest are children, and in order to ease the pain in the patients and, at the same time, thereby assuring compliance, it naturally is desired that the injectable solution itself would cause no pain. There is so far no preparation actually used in treatment and that causes no pain in the patients upon infusion of the composition. Therefore, in light of pain upon infusion, further room for an improvement is left in any of the preparations described in the above CABI publication and the Genentech publication (the latter describes citrate buffer as being preferable), as well as in the preparation according to the above patent application by the present inventors. Elimination or reduction of pain would be beneficial to the patients.

The first objective of the present invention is to solve the above stability problems of a hGH aqueous preparation for injection, i.e., to provide a stable hGH aqueous preparation in which deamination, polymerization and aggregation are sufficiently suppressed and formation of the above fine particle is also suppressed.

Another objective of the present invention is provide a hGH aqueous preparation with which pain due to its composition felt during infusion in subcutaneous or intramuscular injection is eliminated or reduced.

With a variety of hGH preparations unintentionally kept in storage before lyophilization, the present inventors found that preparations obtained by dissolving hGH in aqueous solutions the pH of which was maintained at 6 with maleate buffer or succinate buffer are comparably stable to the solution (described in Unexamined Patent Publication No. 92125/1996) in which the same pH was kept by means of citrate buffer, and that they do not produce dimers or polymers, nor do they produce deamidated products. The tests conducted and best reflecting changes in the quality of human growth hormone were: determination of monomer content on size-elimination high performance liquid chromatography (SE-HPLC), determination of the content of deamination products using high-performance liquid chromatography using a reverse-phase column, observation of general appearance and pH measurement. As a result of further intense examinations on the aqueous preparations during production, under conditions with thermal stress and after 6-month storage in cool place, maleate buffer, succinate buffer and citrate buffer were selected as having proper buffering ability out of pyruvate buffer, acetate buffer, phosphate buffer, citrate buffer, succinate buffer and maleate buffer.

It was confirmed again that by employing those proper buffers stabilization of hGH could be achieved at slightly or weakly acidic pH. However, closer observation revealed that slightly visible fine particles which scatter light and are distinguished from aggregates were detectable when preparations had been made under slightly to weakly acidic conditions. Therefore, we examined the effect of a number of compounds in search of a method to suppress the formation of the fine particles. As a results, we discovered that a low concentration of benzalkonium chloride can effectively suppress the formation of the fine particles. Further studies were carried out on the basis of this finding and it was made clear that a stable hGH aqueous preparation, in which deamination, polymerization and aggregation, as well the fine particle formation is suppressed, can be produced by employing certain formulations of aqueous preparation according to which hGH is dissolved in a solution adjusted to slightly to weakly acidic pH and containing benzalkonium chloride. The present invention was thus completed.

Meanwhile, further studies of such slightly to weakly acidic aqueous preparations led to an unexpected finding that while citrate used as a buffering agent for maintaining this pH range caused substantial pain in subcutaneous injection when the solution was infused, maleate or succinate, which are similar polycarboxylic acid salts, in contrast caused no pain substantially. On the basis of this finding, a preferable hGH-containing aqueous pharmaceutical composition has been successfully prepared which has good stability and causes no pain upon infusion.

SUMMARY OF THE INVENTION

Thus, the present invention provides an aqueous pharmaceutical composition for injection comprising human growth hormone wherein said human growth hormone is dissolved in a benzalkonium chloride-containing, slightly to weakly acidic buffered solution.

The slightly to weakly acidic pH is preferably equal to or greater than 5 and lower than 7, more preferably 5.5–6.5, further more preferably 5.75–6.25, and particularly preferably about pH6.

From the viewpoint of stability, the amount of benzalkonium chloride to be contained in the composition of the present invention may be determined within a wide range as long as the formation of fine particles can be suppressed both during preparation and long-term storage. However, the amount is preferably 0.002–0.03 mg per ml, which is the amount allowed for pharmaceutical preparations for subcutaneous or intramuscular injection, and more preferably 0.005–0.02 mg per ml.

As to buffering agents, those that are suitable to adjust the pH to lower than 7, preferably not more than 6.5, and having buffering ability to keep the pH above a lower limit that would not cause hGH precipitation. Such buffers may be advantageously used that have buffering action preferably within a range of pH5 to less than 7, more preferably 5.5–6.5. Examples of especially preferred buffering agents include maleate, succinate and citrate.

While there is no particular limitation with regard to concentration of a buffering agent as far as the buffering ability is retained, the concentration is usually 1–100 mM, more preferably 1–50 mM, further more preferably 2–20 mM. In the present specification, the term "concentration" when referred to in relation to a buffering agent is meant to indicate the total concentration of the chemical species consisting of the free organic acid that constitute the buffer and all the conjugate bases that are formed by its primary or further dissociation.

Among these buffering agents, maleate and succinate are especially advantageous as they will cause no substantial pain attributable to the composition of the solution upon subcutaneous or intra-muscular infusion of the composition according to the present invention. In particular, maleate is most preferable as it has an abundance of experiences used as a buffering agent for subcutaneous and intramuscular injections.

Therefore, the present invention further provide an aqueous pharmaceutical composition for injection comprising human growth hormone wherein said human growth hormone is dissolved in a benzalkonium chloride-containing, slightly to weakly acidic buffered solution, and wherein maleate or succinate, particularly preferably maleate, is used as the buffering agent, said composition thereby made less painful when infused. Such a composition can not only retain higher stability of hGH but also greatly ease pain felt by the patients on each administration, thus having further advantage.

DETAILED DESCRIPTION OF THE INVENTION

In the present invention, the term "human growth hormone" or its abbreviation "hGH" includes natural-type hGH consisting of 191 amino acids. Its origin is not limited and it may therefore be obtained through any route such as by genetic recombination technique or extraction from the pituitary gland. Moreover the term further includes a physiologically active type having N-terminal methionine and consisting of 192 amino acids as is obtained by gene recombination, as well as other variants in which some of the amino acids are deleted, substituted or added but having substantially comparable activity to the natural-type human growth hormone.

There is no particular limitation with regard to the amount of human growth hormone contained in the composition of the present invention. Thus, its upper limit may be the utmost amount that can be dissolved in the buffer solution employed and the lower limit may be any of the amount that is common among the preparation. Preferably, the amount of human growth hormone is up to about 10 mg per ml, the amount commonly adopted in these preparations.

In the production of the composition of the present invention, benzalkonium chloride may be used in either liquid form of solid one insofar as it is of allowable grade as an additive to pharmaceutical products.

The osmotic pressure of injections is particularly important in subcutaneous and intramuscular injection and therefore care must be taken. Injectable solutions, when hypotonic or hypertonic, would cause pain upon infusion. Usually, it is recommended that the relative osmolarity of an injectable solution be 0.9–1.6, more preferably 1.0–1.4, in comparison with physiological saline.

D-mannitol and neutral salts may be included, singularly or in combination, so that the composition of the present invention is adjusted to this relative osmolarity. D-mannitol may be included to make the relative osmolarity of 0.9–1.6, preferably 1.0–1.4, provided that its amount is 30–100 mg per ml of the composition of the present invention. Further, neutral salts, e.g. sodium chloride, may be included to make the relative osmolarity of 0.9–1.6, preferably 1.0–1.4, provided that its amount is 5–20 mg per ml of the composition of the present invention.

Because the dosage of hGH used as a pharmaceutical product is at present regulated to be 0.5 [IU] per kg body weight per week, its lyophilized preparation is sometimes injected portionwise over several times. Because of this, preservatives are often added in order to prevent contamination with bacteria and the like during storage.

It is also allowed to add preservatives to the composition of the present invention in the amount that does not affect the quality of the hGH and exhibits the preservative effect. In general, sodium benzoate is first recommended as a suitable preservative for the composition of the present invention, but benzoic acid, phenol and the like may also be used. Addition of benzyl alcohol, metacresol and methyl p-hydroxybenzoate, which are generally employed in those lyophilized hGH preparations that require dissolution prior to use, are not recommended to the composition of the present invention as they tend to cause a somewhat accelerated formation of deamidation products compared with addition of sodium benzoate, benzoic acid or phenol. The amount of a preservative may be conveniently adjusted with reference to the usually employed amount in injections. For sodium benzoate, the amount may be, for example, 0.1–5 mg, preferably 0.5–3 mg per ml of the composition of the present invention.

The composition of the present invention may contain a nonionic surfactant. A nonionic surfactant, e.g. polysorbate 20 or polysorbate 80, when added in an amount of 0.5–5 mg, more preferably 1–2 mg per ml of the composition of the present invention, can further enhance the stability, though slightly.

The production of the composition of the present invention may be conducted following conventional procedures for production of aqueous injections. The composition of the present invention is preferably kept in cool storage, particularly at 2–8° C.

As it is an aqueous solution, the composition of the present invention can be supplied in a more convenient form than the usual preparations requiring dissolution prior to use. While filling of the composition into supply containers may be conducted by a conventional method for production of single-solution-type injections, it is preferred to leave no air bubble behind after filling in order to reduce the influence of shaking during storage to thereby further ensure stability.

Stability Tests

Formation of dimers, polymers and deamidated products are well known alteration occurring in hGH. The former two can be determined by size-elimination HPLC (SE-HPLC), and the latter by reverse-phase HPLC (RP-HPLC). In addition, physicochemical determination of its content using a reference standard with known biological activity is accepted as a proper alternative determination method to the hGH biological assay, for there has been observed correlation between peak area of monomer detected on size-elimination HPLC of hGH and its biological activity (Yuki et al., Iyakuhin Kenkyu, 25: 383 (1994)). Therefore, the evaluation of hGH using these two HPLC's provides not only evaluation of monomer and deamidated products, but also determination of biological activity of hGH.

The present inventors examined the stability of the hGH aqueous preparation of the present invention by these methods of determination. As a result, while gradual formation of deamidation products were detected, calculation on the basis of the results obtained after storage at 30° C. and 40° C. revealed that the amount of deamidation products can be confined within 12% for a year under a storage condition of 4° C., pH 5.5–6.5. In addition, it was also revealed that the monomer content can be maintained at 98% or more after one-year storage at 4° C. These results indicate that the hGH aqueous pharmaceutical composition according to the present invention can be supplied as a product under a condition of being stored in cool place, and without lyophilization, which is required by the conventional products. The details of the stability studies are described below.

Determination Methods

The size-elimination HPLC and the reverse-phase HPLC were carried out in accordance with the method by Yuki et al.(Iyakuhin Kenkyu, 25: 383 (1994)).

1. Size-elimination HPLC (SE-HPLC): The following column and conditions were employed.
    (1) Column: TSK gel G3000SW$_{XL}$ (7.8 mm×30 cm)
    (2) Eluant: 0.2 M sodium phosphate buffer (pH 6.5), 0.2 M sodium chloride.
    (3) Flow rate: 0.6 ml/min, Column Temp.: room temperature, Detection wavelength: 280 nm 2. Reverse-phase HPLC (RP-HPLC): The following column and conditions were employed.
    (1) Column: Vydac 214TP54 (4.6 mm×25 cm)
    (2) Eluant: 50 mM Tris-HCl buffer (pH 7.5):n-propanol= 71:29
    (3) Flow rate: 0.5 ml/min, Column Temp.: 45° C., Detection wavelength: 280 nm Test Example 1
Buffer Solution 1

A 20 mM citrate buffer containing, per ml, 0.02 mg of benzalkonium chloride and 100 mg of D-mannitol (pH 6.0).

Buffer Solution 2

A 20 mM citrate buffer containing, per ml, 100 mg of D-mannitol (pH 6.0).

Buffer Solution 3

A 20 mM maleate buffer containing, per ml, 0.02 mg of benzalkonium chloride and 100 mg of D-mannitol (pH 6.0).

Buffer Solution 4

A 20 mM maleate buffer containing, per ml, 100 mg of D-mannitol (pH 6.0).

Buffer Solution 5

A 20 mM succinate buffer containing, per ml, 0.02 mg of benzalkonium chloride and 100 mg of D-mannitol (pH 6.0).

Buffer Solution 6

A 20 mM succinate buffer containing, per ml, 100 mg of D-mannitol (pH 6.0).

To each of the above six buffer solutions was added an equal volume of a 6.8 mg/ml natural-type hGH aqueous solution and gently mixed to give aqueous compositions 1–6, respectively (final pH 6). Then, each of the solutions was passed through a filter with a pore size of 0.22 μm and drawn into needled syringes by 1 ml each, removed of air babbles and then sealed to give samples.

A portion of each of the above aqueous preparations was subjected to horizontal shaking (amplitude 20 mm, 220 cycles/min) at 2–8° C. for 24 hours. Table 1. shows the results.

Out of the aqueous preparations, in aqueous preparations 2, 4 and 6, any of which included no benzalkonium chloride, a trace amount of fine particles were noticed to form during dispensation into the syringes and sealing. The amount of the fine particles increased by shaking. In contrast, in aqueous preparations 1,3 and 5, to which benzalkonium chloride had been added, no formation of fine particles was observed during dispensation and sealing, and, moreover, formation of fine particles was suppressed even in vigorous shaking. As for monomer content as determined by SE-HPLC or the amount of deamidation products as determined by RP-HPLC, no difference was observed between pre- and post-shaking, and the addition of benzalkonium chloride caused no difference, either. The results indicate that benzalkonium chloride is an effective stabilizer for suppressing fine particle formation in hGH-containing aqueous preparations.

TABLE 1

Relation between stability and presence of benzalkonium chloride in buffer solutions.

| | During dispentsation and sealing | | | After 24-hour shaking | | |
|---|---|---|---|---|---|---|
| Aqueous preparation | Monomer content (%) | Amount of deamidation product | General appearance | Monomer content (%) | Amount of deamidation product (%) | General appearance |
| 1 | 99.1 | 2.9 | Colorless and clear, No fine particles | 99.1 | 3.0 | Colorless and clear, No fine particles |
| 2 | 99.2 | 2.9 | Colorless and clear, Fine particles slightly observed | 99.2 | 3.1 | Colorless and clear, Fine particles increased |
| 3 | 99.2 | 2.8 | Colorless and clear, No fine particles | 99.2 | 2.9 | Colorless and clear, No fine particles |
| 4 | 99.2 | 2.8 | Colorless and clear, Fine particles slightly observed | 99.2 | 2.9 | Colorless and clear, Fine particles increased |

TABLE 1-continued

Relation between stability and presence of benzalkonium chloride in buffer solutions.

| Aqueous preparation | During dispentsation and sealing | | | After 24-hour shaking | | |
|---|---|---|---|---|---|---|
| | Monomer content (%) | Amount of deamidation product | General appearance | Monomer content (%) | Amount of deamidation product (%) | General appearance |
| 5 | 99.1 | 2.5 | Colorless and clear, No fine particles | 99.1 | 2.7 | Colorless and clear, No fine particles |
| 6 | 99.2 | 2.4 | Colorless and clear, Fine particles slightly observed | 99.1 | 2.6 | Colorless and clear, Fine particles increased |

Test Example 2

To each of 20 mM citrate buffer (pH 6.0) and maleate buffer (pH 6.0), both containing 0.002–0.1 mg per ml of benzalkonium chloride and 100 mg/ml of D-mannitol, was added an equal volume of a 6.8 mg/ml natural-type hGH aqueous solution, and gently mixed (final pH 6.0). Each of the solutions was passed through a filter with a pore size of 0.22 μm and drawn into needled syringes by 1 ml each, removed of air babbles and then sealed. They were evaluated based on their general appearance and the amount was determined of benzalkonium chloride required for effective suppression of fine particle formation. The results were as shown in Table 2. The suppression effect was observed when the amount of amount of benzalkonium chloride was 0.002–0.03 mg per ml of the preparations.

TABLE 2

Relation between benzalkonium chloride concentration and suppression of fine particle formation

| Concentration of benzalkonium chloride (mg/ml) | Citrate buffer General appearance | Maleate buffer General appearance |
|---|---|---|
| 0.05 | slightly cloudy | Colorless and clear, No fine particles |
| 0.03 | Colorless and clear, No fine particles | Colorless and clear, No fine particles |
| 0.02 | Colorless and clear, No fine particles | Colorless and clear, No fine particles |
| 0.01 | Colorless and clear, No fine particles | Colorless and clear, No fine particles |
| 0.005 | Colorless and clear, No fine particles | Colorless and clear, No fine particles |

TABLE 2-continued

Relation between benzalkonium chloride concentration and suppression of fine particle formation

| Concentration of benzalkonium chloride (mg/ml) | Citrate buffer General appearance | Maleate buffer General appearance |
|---|---|---|
| 0.002 | Colorless and clear, No fine particles | Colorless and clear, No fine particles |
| 0.001 | Colorless and clear, Fine particles observed | Colorless and clear, Fine particles observed |
| 0 | Colorless and clear, Fine particles observed | Colorless and clear, Fine particles observed |

Test Example 3

Each of the aqueous preparations 1,3 and 5 in Test Example 1 above was stored in incubators at 40° C. and 50° C. for 0, 3, 7, 10, 14 and 21 days, and then removed of the seal and analyzed on RP-HPLC and SE-HPLC. The results are shown in Table 3. Calculation on the results of RP-HPLC in accordance with an equation for stability estimation revealed that, although there would occur gradual formation of deamidation products, these preparations are stable for at least one year, when a provisional upper limit for deamidation products is set at 12%. On the other hand, from the result of the SE-HPLC analysis, it was concluded that the monomer content could be maintained equal to or greater than 98% even after one year storage at 2–8° C. From the comparison of samples taken at points along the storage period, no difference was observed among those types of buffers in either results from these HPLC determination.

TABLE 3

Stability of aqueous preparations 1, 3 and 5 after storage at 40° C. and 50° C.

| Aqueous preparation | Monomer content (%) (SE-HPLC) | | | | Amount of deamidation product (%) (RP-HPLC) | | | |
|---|---|---|---|---|---|---|---|---|
| | Initial | 7 days | 14 days | 21 days | Initial | 7 days | 14 days | 21 days |
| Storage at 40° C. | | | | | | | | |
| 1 | 99.1 | 99.1 | 99.1 | 99.0 | 2.9 | 13.4 | 22.7 | 28.9 |
| 3 | 99.2 | 99.3 | 99.2 | 99.0 | 2.8 | 13.5 | 22.6 | 28.9 |
| 5 | 99.1 | 99.0 | 98.8 | 98.8 | 2.5 | 13.3 | 23.0 | 28.7 |

TABLE 3-continued

Stability of aqueous preparations 1, 3 and 5 after storage at 40° C. and 50° C.

| Aqueous preparation | Monomer content (%) (SE-HPLC) | | | | Amount of deamidation product (%) (RP-HPLC) | | | |
|---|---|---|---|---|---|---|---|---|
|  | Initial | 7 days | 14 days | 21 days | Initial | 7 days | 14 days | 21 days |
| Storage at 50° C. | | | | | | | | |
| 1 | 99.1 | 98.8 | 98.5 | 98.3 | 2.9 | 29.7 | 36.3 | 38.9 |
| 3 | 99.2 | 99.0 | 98.9 | 98.6 | 2.8 | 29.9 | 36.5 | 39.1 |
| 5 | 99.1 | 98.8 | 98.3 | 97.5 | 2.5 | 30.0 | 36.5 | 39.0 |

Test Example 4
Buffer Solution 7
A 20 mM citrate buffer containing, per ml, 0.02 mg of benzalkonium chloride and 100 mg of D-mannitol (pH 6.0).
Buffer Solution 8
A 20 mM maleate buffer containing, per ml, 0.02 mg of benzalkonium chloride and 100 mg of D-mannitol (pH 6.0).
Buffer Solution 9
A 20 mM succinate buffer containing, per ml, 0.02 mg of benzalkonium chloride and 100 mg of D-mannitol (pH 6.0).

To each of the above three buffer solutions was added an equal volume of a 6.8 mg/ml natural-type hGH aqueous solution and gently mixed to give aqueous compositions 7–9, respectively (final pH 6). Then each of the solutions was passed through a filter with a pore size of 0.22 μm and drawn into needled syringes by 1 ml each, removed of air babbles and then sealed to give samples. Each aqueous solution was put in storage for 6 months at 2–8° C. and samples were checked for change in monomer content, amount of deamidation products and general appearance after 0, 1, 3 and 6-month storage. The results are shown in Table 4. No formation of fine particles was observed in any of these aqueous preparation.

TABLE 4

Results with aqueous preparations 7–9 stored for 6 months at 2–8° C.

| Aqueous preparation | Monomer content (%) (SE-HPLC) | | | | Amount of Deamidation product (%) (RP-HPLC) | | | |
|---|---|---|---|---|---|---|---|---|
|  | Initial | 1 month | 3 months | 6 months | Initial | 1 month | 3 months | 6 months |
| 7 | 99.0 | 99.0 | 99.0 | 99.1 | 2.4 | 2.4 | 3.7 | 4.2 |
| 8 | 99.2 | 99.3 | 99.1 | 99.0 | 2.3 | 2.3 | 3.6 | 4.0 |
| 9 | 99.1 | 99.0 | 98.9 | 98.8 | 2.4 | 2.5 | 3.7 | 4.3 |

Test Example 5
Test for Pain Upon Infusion
For evaluation of pain felt upon subcutaneous infusion which is attributable to the composition, injectable preparations were made by the addition of D-mannitol to each of a citrate, maleate or succinate buffer (final pH 6.0) in such a proper amount that would give a relative osmolarity of 1.1 compared with physiological saline. hGH, however, was not added because the purpose of the test was to examine the pain attributable to buffer types. After adequate explanation of the test purpose, the test was conducted on ten healthy male volunteers for the strength of pain upon infusion of the following three preparations. The tests of these preparations were conducted in blind fashion. The strength of pain was expressed by; (++) as being very painful, (+) painful, (±) could be said painful, (−) not painful.

Formula 1: 10 mM citrate buffer+D-mannitol (pH 6.0)
Formula 2: 10 mM maleate buffer+D-mannitol (pH 6.0)
Formula 3: 10 mM succinate buffer+D-mannitol (pH 6.0)

TABLE 5

Relation of pain upon infusion and the type of buffer (10 for each group)

| Formula | (++) | (+) | (±) | (−) |
|---|---|---|---|---|
| Formula 1 | 10 | 0 | 0 | 0 |
| Formula 2 | 0 | 0 | 0 | 10 |
| Formula 3 | 0 | 0 | 1 | 9 |

The results are shown in Table 5. Figures in the table indicate the number of the subjects who gave the corresponding judgement. While all of the ten subjects judged the citrate based preparation as being "very painful", all the subjects judged the maleate based preparation as being "not painful". In addition, succinate based preparation was judged as being "not painful" by 9 subjects out of 10 and judged as "could be painful" by one subject. These results have revealed that there is felt little or no pain with maleate or succinate based preparations, in contrast with citrate based preparations, which cause strong pain upon infusion.

Test Example 6
Buffer Solution 10
A 20 mM citrate buffer containing, per ml, 0.02 mg of benzalkonium chloride, 50 mg of D-mannitol, 5 mg of sodium chloride and 2 mg of sodium benzoate (pH 6.0).
Buffer Solution 11
A 20 mM maleate buffer containing, per ml, 0.02 mg of benzalkonium chloride, 50 mg of D-mannitol, 5 mg of sodium chloride and 2 mg of sodium benzoate (pH 6.0).
Buffer Solution 12
A 20 mM succinate buffer containing, per ml, 0.02 mg of benzalkonium chloride, 50 mg of D-mannitol, 5 mg of sodium chloride and 2 mg of sodium benzoate (pH 6.0).

To each of the above three buffer solutions was added an equal volume of a 6.8 mg/ml natural-type hGH aqueous solution and gently mixed to give aqueous compositions 10–12, respectively (final pH 6). Then each of the solutions was passed through a filter with a pore size of 0.22 μm and drawn into needled syringes by 1 ml each, removed of air babbles and then sealed to give samples. Each aqueous solution was put in stored at 40° C. and 50° C., opened after 21 days, and then analyzed on RP-HPLC and SE-HPLC. The results are shown in Table 6.

TABLE 6

Results of analyses of aqueous preparations 10–12

| Aqueous preparation | Monomer content (%) (SE-HPLC) | | | | Amount of deamidation product (%) (RP-HPLC) | | | |
|---|---|---|---|---|---|---|---|---|
| | 40° C. | | 50° C. | | 40° C. | | 50° C. | |
| | Initial | After 21 days | Initial | After 21 days | Initial | After 21 days | Initial | After 21 days |
| 10 | 99.2 | 99.1 | 99.2 | 98.5 | 2.3 | 28.0 | 2.3 | 38.1 |
| 11 | 99.4 | 99.2 | 99.4 | 98.5 | 2.3 | 27.9 | 2.3 | 37.9 |
| 12 | 99.2 | 98.9 | 99.2 | 98.0 | 2.4 | 28.0 | 2.4 | 38.3 |

In any of the aqueous preparations, change in monomer content was very little after storage of 21 days at 40 and 50° C. Formation of deamidation products, on the other hand, was within limits of the expected long-term stability as mentioned in Test Example 3 above, i.e., enough to predict one-year stability.

Test Example 7
Buffer Solution 13

A 20 mM maleate buffer containing, per ml, 0.02 mg of benzalkonium chloride and 100 mg of D-mannitol (pH 6.0).

To the above buffer solution 13 was added an equal volume of a 20.4 mg/ml natural-type hGH aqueous solution and gently mixed to give aqueous preparation 13 (final pH 6.0). Then the solution was passed through a filter with a pore size of 0.22 μm and drawn into needled syringes by 1 ml each, removed of air babbles and then sealed to give samples. The aqueous preparation 13 was put in storage in incubators at 40° C. and 50° C., opened after 21 days, and then analyzed on RP-HPLC and SE-HPLC. The results are shown in Table 7.

TABLE 7

Stability of aqueous preparation 13

| Aqueous preparation | Monomer content (%) (SE-HPLC) | | | | Amount of deamidation product (%) (RP-HPLC) | | | |
|---|---|---|---|---|---|---|---|---|
| | 40° C. | | 50° C. | | 40° C. | | 50° C. | |
| | Initial | After 21 days | Initial | After 21 days | Initial | After 21 days | Initial | After 21 days |
| 13 | 99.2 | 98.8 | 99.2 | 97.1 | 2.2 | 28.5 | 2.2 | 39.6 |

The preparation showed little change in monomer content after 21-day storage at 40° C. and 50° C. Formation of deamidation products, on the other hand, was within limits of the expected long-term stability as mentioned in Test Example 1 above, i.e., enough to predict one-year stability

EXAMPLES

The present invention is described in further detail below with reference to typical examples. It should be noted, however, that the present invention is not limited by these examples. It is possible to increase or decrease the amount or concentration of each of the components set forth in the examples below, to substitute one ore more of their components with other components, or to include additional components.

Example 1

The components is admixed in accordance with the following formula to form a buffer solution, then added with the hGH solution described below, and sterilized by filtration to give an injectable preparation (final pH 6.0).

Buffer Solution

| Benzalkonium chloride | 0.02 mg |
|---|---|
| D-mannitol | 100 mg |
| 20 mM citrate buffer | q.s. |
| Total amount | 1 ml (pH 6.0) | hGH Solution 6.8 mg/ml natural-type hGH aqueous solution . . . 1 ml

Example 2

An injectable preparation is formed according to the formula below following the same procedure as Example 1 (final pH 6.0).

Buffer Solution

| Benzalkonium chloride | 0.02 mg |
|---|---|
| D-mannitol | 100 mg |
| 20 mM maleate buffer | q.s. |
| Total amount | 1 ml (pH 6.0) | hGH Solution 6.8 mg/ml natural-type hGH aqueous solution . . . 1 ml

Example 3

An injectable preparation is formed according to the formula below following the same procedure as Example 1 (final pH 6.0).
Buffer Solution

| | |
|---|---|
| Benzalkonium chloride | 0.02 mg |
| D-mannitol | 100 mg |
| 20 mM succinate buffer | q.s. |
| Total amount | 1 ml (pH 6.0) | hGH Solution
  6.8 mg/ml natural-type hGH aqueous solution . . . 1 ml

Example 4

An injectable preparation is formed according to the formula below following the same procedure as Example 1 (final pH 6.0).
Buffer Solution

| | |
|---|---|
| Benzalkonium chloride | 0.02 mg |
| D-mannitol | 50 mg |
| Sodium chloride | 5 mg |
| Sodium benzoate | 2 mg |
| 20 mM citrate buffer | q.s. |
| Total amount | 1 ml (pH 6.0) | hGH Solution
  6.8 mg/ml natural-type hGH aqueous solution . . . 1 ml

Example 5

An injectable preparation is formed according to the formula below following the same procedure as Example 1 (final pH 6.0).
Buffer Solution

| | |
|---|---|
| Benzalkonium chloride | 0.02 mg |
| D-mannitol | 50 mg |
| Sodium chloride | 5 mg |
| Sodium benzoate | 2 mg |
| 20 mM maleate buffer | q.s. |
| Total amount | 1 ml (pH 6.0) | hGH Solution
  6.8 mg/ml natural-type hGH aqueous solution . . . 1 ml

Example 6

An injectable preparation is formed according to the formula below following the same procedure as Example 1 (final pH 6.0).
Buffer Solution

| | |
|---|---|
| Benzalkonium chloride | 0.02 mg |
| D-mannitol | 50 mg |
| Sodium chloride | 5 mg |
| Sodium benzoate | 2 mg |
| 20 mM succinate buffer | q.s. |
| Total amount | 1 ml (pH 6.0) | hGH Solution
  6.8 mg/ml natural-type hGH aqueous solution . . . 1 ml

Example 7

An injectable preparation is formed according to the formula below following the same procedure as Example 1 (final pH 6.0).
Buffer Solution

| | |
|---|---|
| Benzalkonium chloride | 0.002 mg |
| D-mannitol | 100 mg |
| 20 mM maleate buffer | q.s. |
| Total amount | 1 ml (pH 6.0) | hGH Solution
  6.8 mg/ml natural-type hGH aqueous solution . . . 1 ml

Example 8

An injectable preparation is formed according to the formula below following the same procedure as Example 1 (final pH 6.0).
Buffer Solution

| | |
|---|---|
| Benzalkonium chloride | 0.01 mg |
| D-mannitol | 100 mg |
| 20 mM maleate buffer | q.s. |
| Total amount | 1 ml (pH 6.0) | hGh Solution
  6.8 mg/ml natural-type hGH aqueous solution . . . 1 ml

What is claimed is:

1. An aqueous pharmaceutical composition for injection comprising human growth hormone dissolved in a solution comprising benzalkonium chloride and a buffering agent selected from maleate, succinate or citrate, said solution further comprising at least one of D-mannitol and sodium chloride, the aqueous composition having a pH which is slightly to weakly acidic.

2. The composition of claim 1 wherein said solution further comprises sodium benzoate.

3. The composition of claim 1 wherein the pH is equal to or greater than 5 and less than 7.

4. The composition of claim 1 wherein the benzalkonium chloride is present in an amount from 0.002 to 0.03 mg per ml of said solution.

5. The composition of claim 1 wherein the concentration of the buffering agent is from 1 to 100 mM of said solution.

6. The composition of claim 5 wherein the concentration of the buffering agent is from 1 to 50 mM of said solution.

7. The composition of claim 6 wherein the concentration of the buffering agent is 2 to 20 mM of said solution.

8. The composition of claim 1 wherein the solution comprises D-mannitol.

9. The composition of claim 8 wherein the content of D-mannitol is from 30 to 100 mg per ml of said solution.

10. The composition of claim 1 wherein the solution comprises sodium chloride.

11. The composition of claim 10 wherein the content of sodium chloride is from 5 to 20 mg per ml of said solution.

12. The composition of claim 1 wherein the solution further comprises a preservative selected from sodium benzoate, benzoic acid or phenol.

13. The composition of claim 12 wherein the preservative is sodium benzoate and is present in an amount from 0.1 to 5 mg per ml of said solution.

14. The composition of claim 1 wherein the solution further comprises a nonionic surfactant, which is present in an amount from 0.5 to 5 mg per ml of said solution.

15. The composition of claim 1 wherein the buffering agent is maleate.

16. An aqueous pharmaceutical composition for injection comprising human growth hormone dissolved in a solution comprising benzalkonium chloride in an amount from 0.002 to 0.03 mg per ml of said composition and a buffering agent in an amount from 1 to 100 mM and selected from maleate, succinate or citrate, wherein the pH of the composition is equal to or greater than 5 and less than 7 and the composition is less painful when injected, the solution further comprising D-mannitol, neutral salt or mixture thereof.

17. The composition of claim 16 wherein the solution further comprises D-mannitol and the content of D-mannitol is from 30 to 100 mg per ml of said solution.

18. The composition of claim 16 wherein the solution further comprises neutral salt and said neutral salt is sodium chloride.

19. The composition of claim 18 wherein the content of sodium chloride is 5 to 20 mg per ml. of said solution.

20. The aqueous pharmaceutical composition of claim 16 wherein the buffering agent is maleate.

21. The aqueous pharmaceutical composition of claim 16 wherein the buffering agent is succinate.

22. A method for injecting an aqueous pharmaceutical composition into a patient in need of human growth hormone therapy comprising injecting into the patient the aqueous pharmaceutical composition comprising the solution of claim 16.

23. The method of claim 22 wherein the buffering agent is maleate.

24. The method of claim 22 wherein the buffering agent is succinate.

25. A method for injecting an aqueous pharmaceutical composition into a patient in need of human growth hormone therapy comprising injecting into the patient the aqueous pharmaceutical composition comprising the solution of claim 1.

26. The method of claim 25 wherein the aqueous solution further comprises a preservative selected from sodium benzoate, benzoic acid or phenol.

27. The method of claim 26 wherein the preservative is sodium benzoate.

28. The method of claim 27 wherein the sodium benzoate is present in an amount from 0.1 to 5 mg per ml of said aqueous solution.

29. The method of claim 25 wherein the pH is equal to or greater than 5 and less than 7.

30. The method of claim 25 wherein the benzalkonium chloride is present in an amount from 0.002 to 0.03 mg per ml. of said solution.

31. The method of claim 25 wherein the concentration of the buffering agent is from 1 to 100 mM of said solution.

32. The method of claim 31 wherein the concentration of the buffering agent is from 1 to 50 mM of said solution.

33. The method of claim 32 wherein the concentration of the buffering agent is 2 to 20 mM of said solution.

34. The method of claim 25 wherein the content of D-mannitol is from 30 to 100 mg per ml. of said solution.

35. The method of claim 25 comprising sodium chloride.

36. The method of claim 35 wherein the content of sodium chloride is from 5 to 20 mg per ml. of said solution.

37. The method of claim 25 further comprising a nonionic surfactant, which is present in an amount from 0.5 to 5 mg per ml of said solution.

38. The method of claim 25 wherein the buffering agent is maleate.

* * * * *